(12) United States Patent
Anderson

(10) Patent No.: US 7,731,992 B2
(45) Date of Patent: Jun. 8, 2010

(54) METHOD OF INHIBITING AROMATASE WITH SPECIFIC DIETARY SUPPLEMENTS

(75) Inventor: Mark L. Anderson, Chester, NY (US)

(73) Assignee: Triarco Industries, Inc., Wayne, NJ (US)

(*) Notice: Subject to any disclaimer, the term of this patent is extended or adjusted under 35 U.S.C. 154(b) by 0 days.

(21) Appl. No.: 10/360,928

(22) Filed: Feb. 10, 2003

(65) Prior Publication Data

US 2004/0156926 A1    Aug. 12, 2004

(51) Int. Cl.
*A01N 65/00* (2006.01)
(52) U.S. Cl. ............................................. 424/725
(58) Field of Classification Search ................. 424/725
See application file for complete search history.

(56) References Cited

U.S. PATENT DOCUMENTS

| | | | |
|---|---|---|---|
| 4,602,025 A | 7/1986 | Hirsch et al. | 514/359 |
| 6,096,307 A | 8/2000 | Braswell et al. | 424/94.1 |
| 6,197,309 B1* | 3/2001 | Wheeler | 424/727 |
| 6,217,878 B1 | 4/2001 | Menon et al. | 424/195.1 |
| 6,242,012 B1* | 6/2001 | Newmark et al. | 424/756 |
| 6,277,417 B1 | 8/2001 | Anderson | 424/727 |
| 6,433,025 B1 | 8/2002 | Lorenz | 514/725 |
| 2003/0008048 A1* | 1/2003 | Winston et al. | 426/548 |
| 2003/0104076 A1* | 6/2003 | Berkulin et al. | 424/725 |

FOREIGN PATENT DOCUMENTS

JP       07041687    *  2/1995
JP    20011342142    * 12/2001

OTHER PUBLICATIONS

Kapadia et al., Pharmacological Research, vol. 45, No. 3, 2002, 213-220.*
Catchpole et al., Journal of Supercritical Fluids, 22 (2002), 129-138.*
Tesch, Clinical Journal of Women's Health, vol. 1, No. 2, Mar. 2001, 89-102.*
Tesch, Dis. Mon., Oct. 2002, 48:671-696.*
HealthCentral.com, Black Cohosh, 3 pages, 2007.*
M. Clemons et al., "Estrogen And The Risk Of Breast Cancer", The New England Journal of Medicine, Med. vol. 344, No. 4, Jan. 25, 2001.
P. Goss et al., "Aromatase Inhibitors in the Treatment and Prevention of Breast Cancer", Journal of Clinical Oncology, vol. 19, No. 3, pp. 881-894, Feb. 1, 2001.
J. E. Rossouw et al., "Risks and Benefits of Estrogen Plus Progestin in Healthy Postmenopausal Women", Writing Group for the Women's Health Initiative Investigators, JAMA, vol. 288, No. 3, pp. 321-333, Jul. 17, 2002.
J.V. Lacey, Jr., et al., "Menopausal Hormone Replacement Therapy and Risk of Ovarian Cancer", JAMA, vol. 288, No. 3, pp. 334-341, Jul. 17, 2002.
S.W. Fletcher et al., "Failure of Estrogen Plus Progestin Therapy for Prevention", JAMA, vol. 288, No. 3, pp. 366-368, Jul. 17, 2002.
K. Noller, Estrogen Replacement Therapy And Risk of Ovarian Cancer, JAMA, vol. 288, No. 3, pp. 368-369, Jul. 17, 2002.
Goodman & Gilman's, The Pharmacological Basis of Therapeutics Ed. Hardman & Limbird, 10th Ed., McGraw Hill, 2001, pp. 1598-1599.
Mera Pharmaeuticals, Inc., "Astaxanthin Safety for Humans", 2002.

* cited by examiner

*Primary Examiner*—Michael V Meller
(74) *Attorney, Agent, or Firm*—Fizpatrick, Cella, Harper & Scinto

(57) ABSTRACT

The activity of the enzyme aromatase is inhibited by administering an aromatase inhibiting amount of a composition comprising at least one of astaxanthin, black cohosh, echinacea, and phytosterols to a subject.

1 Claim, No Drawings

METHOD OF INHIBITING AROMATASE WITH SPECIFIC DIETARY SUPPLEMENTS

BACKGROUND OF THE INVENTION

1. Field of the Invention

The present invention is directed to compositions and methods of inhibiting the activity of the enzyme aromatase with dietary supplements. In particular, the invention is directed to compositions and methods of inhibiting the activity of aromatase using a composition comprising at least one of the dietary supplements astaxanthin, black cohosh, echinacea, and phytosterols.

2. Related Background Art

There is evidence that estrogen and related estrogenic compounds have a role in the development of cancers in women, in particular, breast cancer. See, for example, Clemons et al., ESTROGEN AND THE RISK OF BREAST CANCER, The New England Journal of Medicine, Vol. 344, No. 4, pp. 276-285 (2001). In addition, it is known that the enzyme aromatase plays a role in the synthesis of estrogen. In particular, aromatase converts $C_{19}$ androgens, such as androstenedione and testosterone, into estrogenic steroids, such as estrone and 17-β estradiol.

Compounds that inhibit the activity of aromatase are known, and have been suggested or used as a treatment for breast cancer. For example, Gross et al., AROMATASE INHIBITORS IN THE TREATMENT AND PREVENTION OF BREAST CANCER, Journal of Clinical Oncology, Vol. 19, No. 3, pp. 881-894 (2001), disclose steroidal and non-steroidal aromatase inhibitors that have been tested in phase III trials as second line treatments of postmenopausal hormone-dependent breast cancer, and may prove superior to tamoxifin. Compounds identified as aromatase inhibitors include aminoglutethimide, a first generation, non-steroidal aromatase inhibitor. Other compounds identified as aromatase inhibitors include the second generation aromatase inhibitors, rogletimide and fadrozol, which are non-steroidal, and formestane, which is steroidal, and the third generation aromatase inhibitors, anastrozole, letrozole, and vorozole, which are non-steroidal, and exemestane, which is steroidal.

Although the third generation inhibitors are less toxic than the first and second generation compounds, they still present toxicity issues. In particular, Goss et al. found that the third generation inhibitors could cause nausea, vomiting, hot flashes, fatigues and headaches. Therefore, a need exists for an aromatase inhibiting composition having lower toxicity than that of prior art aromatase inhibiting compositions. The present invention provides such compositions and a method of inhibiting aromatase with the compositions of the invention.

SUMMARY OF THE INVENTION

The present invention is directed to a composition and a method of inhibiting the activity of the enzyme aromatase. The method of the invention comprises administering an aromatase inhibiting amount of a dietary supplement composition comprising at least one of astaxanthin, black cohosh, echinacea, and phytosterols to a subject. Aromatase inhibiting compositions of the invention preferably comprise an aromatase inhibiting amount of at least two of astaxanthin, black cohosh, echinacea, or phytosterols. More preferably, the aromatase inhibiting compositions of the invention comprise astaxanthin and at least one of black cohosh, echinacea, and phytosterols.

DETAILED DESCRIPTION OF THE INVENTION

The present invention is directed to aromatase inhibiting compositions comprising at least one dietary supplement selected from the group consisting of astaxanthin, black cohosh, echinacea, and phytosterols in an amount sufficient to inhibit aromatase activity in a subject. At the time of the present invention, Applicant was not aware of any disclosure or suggestion that any of those compounds inhibited aromatase activity.

Astaxanthin is a red carotenoid of formula

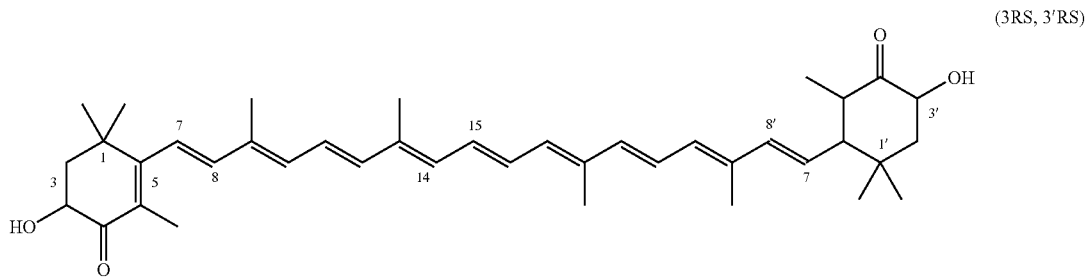

having a toxicity that is significantly lower than prior art aromatase inhibitors. Astaxanthin is synthesized by certain plants and algae, such as the microalgae *Hameatoccus pluvalis*, and occurs naturally in certain animals, such as shrimp, crawfish, crabs, and salmon. Those animals ingest astaxanthin in their own food, and accumulate the carotenoid in their flesh, which gives the animals their distinctive red color.

Astaxanthin is a known antioxidant, exhibiting strong free radical scavenging activity, and preventing lipid peroxidation and oxidative damage of LDL-cholesterol, cells, cell membranes, and tissues. In addition, U.S. Pat. No. 6,277,417 to Anderson discloses a composition comprising astaxanthin that inhibits the activity of 5α-reductase, and provides a method for preventing benign prostate hyperplasia.

*Haematococcus pluvialis* microalgae is a natural source of astaxanthin. The microalgae also contains fatty acids, such as palmitic, oleic, linoleic and stearic acids, protein, minerals, carbohydrates and vitamins. In the practice of the methods of this invention, astaxanthin from any source, whether natural or synthetic, can be used. Synthetic methods for preparing astaxanthin are known (R. D. G. Cooper et al., J. Chem Soc.

Perkins Trans. I, (1975) p. 2195; F. Kienzle, H. Mayer, Helv. Chim. Acta., (1978) Vol. 61, p. 2609), as are methods of isolating astaxanthin from natural sources (Tischer, Z. Physiol. Chem., (1941) Vol. 267 p. 281; Seybold and Goodwin, Nature, (1959) Vol. 184, p. 1714). *Haematococcus pluvialis* microalgae is a preferred natural, commercially available source of the astaxanthin used in the methods of this invention. Thus, astaxanthin can be administered in a pure form as synthesized or isolated from natural sources. For example, astaxanthin may be used in the form of astaxanthin 10 percent oleoresin, which is a supercritical fluid extraction of *Haemotococcus pluvialis* microalgae containing 10 percent astaxanthin, or as astaxanthin 5 percent spray dried, which is a natural or synthetic astaxanthin that is spray dried onto a water-soluble polysaccharide, such as maltodextrin, e.g., Lodex 10, available from Cerestar Co., Hammond, Ind.

Alternatively, astaxanthin may be administered as part of a composition comprising protein, carbohydrate, and fatty acids. When *Haemotococcus pluvialis* algae meal is used as the source of astaxanthin, the composition is preferably administered as derived from the microalgae, comprising the natural protein, carbohydrate, and fatty acid components of the microalgae. Such microalgae is commercially available from Cyanotech Corporation, Kailua-Kona, Hi., and generally comprises as major components from about 1.5 to about 2 percent astaxanthin, from about 15 to about 30 protein, from about 35 to about 40 percent carbohydrates, from about 10 to about 25 percent ash, from about 5 to about 20 percent fat, and from about 3 to about 10 percent moisture, where all amounts are percent by weight. The composition further comprises minor components including iron, magnesium, calcium, biotin, L-carnitine, folic acid, niacin, pantothenic acid, and vitamins B1, B2, B6, B12, C, and E.

Black cohosh, *Cimicifuga racemosa*, a perennial plant native to North America and Canada, contains triterpene glycosides, such as cimicifugoside, acein, and racemoside, isoflavones, such as formononetin, aromatic acids, such as isoferulic and salicylic acids, resin, tannins, and fatty acids as active ingredients. Historically, it has been used as an anti-inflammatory and sedative in treating female reproductive complaints, such as painful menstrual cramping, delayed periods, mastitis, ovarian pain and other menopausal symptoms. Black cohosh also has peripheral vasodilatory and anti-inflammatory effects, and has been used as a remedy for rheumatism and the relief of pain and irritation. Black cohosh has also been used as an alternative to estrogen replacement therapy for those patients in whom estrogen replacement therapy is either refused or contraindicated. Black cohosh may be used in several forms, including a powder of the ground root and as black cohosh PE 4:1, a hydro-alcohol extract of black cohosh root, spray dried onto a water-soluble polysaccharide, such as maltodextrin, to yield a 4:1 weight/weight concentrated product.

Echinacea contains numerous phytochemicals, including caffeic acid derivatives, such as, cichoric acid, alkamides, such as dodecatetraenoic acid, isobutylamides, and glycoproteins/polysaccharides, that are believed to have immunomodulatory and other beneficial activities. Traditionally, echinacea preparations have been used in the adjuvant therapy of inflammations, skin damage, and, more typically, infections. The echinacea plant is popularly used as an herbal immunostimulant. Reportedly, the ability of echinacea to stimulate the immune system in a nonspecific manner is exemplified in the enhancement of phagocytosis seen in cells treated with echinacea. Echinacea's immunomodulatory activity has been attributed to various actives, including alkylamides, phenolics, polysaccharides, alkaloids, glycoproteins, and flavonoids.

Echinacea extract may be obtained from the following echinacea species: *Echinacea angustifolia, Echinacea purpurea*, and *Echinacea pallida. Echinacea angustifolia*, often called purple cornflower, is native to North America. Native Americans have used extracts from this plant for wound healing, and as an anti-inflammatory agent. Freshly squeezed juices of leaves and roots from this plant have been approved by the German government for the treatment of recurrent infections of respiratory and urinary tracts. Liquid echinacea preparations reportedly have immune stimulatory activity when administered orally or parenterally. It is believed that the activation of splenocytes may contribute to the extract's ability to enhance the activity of granulocytes and phagocytes. Echinacea extract has also been used as an anti-AIDS agent. Echinacea extracts, particularly extracts of *Echinacea angustofolia*, reportedly stimulate the production of granulocytes, macrophages, leukocytes and lymphocytes, and are believed to inhibit both viral and bacterial activity.

Phytosterols are found in plants, and have structures similar to cholesterol. They play a role in plants similar to that of cholesterol in humans and mammals, i.e., they participate in the formation of cell membrane structures. Phytosterols comprise plant sterols and plant stanols, as well as their respective esters with fatty acids. The most common plant sterols are β-sitosterol, campesterol and stigmasterol, which are structurally very similar to cholesterol. Plant stanols are the hydrogenated counterparts of the respective plant sterols, e.g. stigmastanol is hydrogenated stigmasterol.

Plant sterols are present in small quantities in many fruits, vegetables, nuts, seeds, cereals, legumes, and other plant sources. Plant stanols occur naturally in even smaller quantities in some of the same sources. For example, both plant sterols and stanols are found in vegetable oils. Plant sterol esters and plant stanol esters may reduce the risk of atherosclerosis and cardiovascular disease by lowering blood cholesterol levels. The consumption of plant sterols and plant stanols reportedly lowers blood cholesterol levels by inhibiting the absorption of dietary cholesterol and bile acids by the small intestine. The plant sterols and stanols are only very poorly absorbed by the body. The inhibition of the absorption of cholesterol and bile acids is related to the similarity in physico-chemical properties of plant sterols or stanols and cholesterol.

Applicant has unexpectedly discovered that a composition comprising at least one dietary supplement selected from the group consisting of astaxanthin, black cohosh, echinacea, and phytosterols can be used to inhibit aromatase activity. As stated above, at the time of the present invention, Applicant was not aware of any disclosure or suggestion that any of those compounds inhibited aromatase activity. A composition for inhibiting aromatase activity preferably comprises astaxanthin and any of black cohosh, echinacea, and phytosterols. More preferably, the composition comprises astaxanthin and black cohosh and, optionally, at least one of echinacea and phytosterols. Most preferably, the composition comprises all four of the dietary supplements astaxanthin, black cohosh, echinacea, and phytosterols.

The method of the invention comprises administering an aromatase inhibiting amount of a composition comprising at least one dietary supplement selected from the group consisting of astaxanthin, black cohosh, echinacea, and phytosterols. A dosage of the aromatase inhibiting composition of the invention may comprise astaxanthin in an amount of at least about 0.1 mg, preferably, from about 1 to about 1,000 mg, and, more preferably, from about 20 to about 500 mg. The black cohosh may be present in an amount of at least 0.1 mg, preferably, from about 1 to about 1,000 mg, and, more preferably, from about 20 to about 500 mg. The echinacea may be present in an amount of at least about 0.1 mg, preferably, from about 1 to about 5,000 mg, and, more preferably, from about 50 to about 100 mg. The phytosterols may be present in an amount of at least about 0.1 mg, preferably, from about 1 to about 5,000 mg, and, more preferably, from about 25 to about 250 mg.

In the practice of the methods of the invention, the aromatase inhibiting dietary supplement composition of the invention may be administered orally in any of the usual solid forms, such as pills, tablets, capsules or powders, including sustained release preparations. The term "unit dosage form", as used herein, refers to physically discrete units to be administered in single or multiple dosage to humans, each unit containing a predetermined quantity of active material, i.e., at least one of astaxanthin, black cohosh, echinacea, and phytosterols, in association with one or more carriers. The quantity of active material is that calculated to produce the desired therapeutic effect upon administration of one or more of such units. Of course, it is understood that the exact treatment level will depend upon the case history of the human subject to be treated. The precise treatment level can be determined by one of ordinary skill in the art without undue experimentation, taking into consideration such factors as age, size, severity of condition, and anticipated duration of administration of compounds, among other factors known to those of ordinary skill.

Unit dosages can range from about 3.0 mg/kg to about 100 mg/kg, where "mg/kg", as used herein, refers to mg of at least one of astaxanthin, black cohosh, echinacea, and phytosterols per kilogram of body weight, preferably from about 10 mg/kg to about 30 mg/kg, most preferably about 20 mg/kg. The doses can be administered in any convenient dosing schedule to achieve the stated beneficial effects. For example, the doses can be taken 1, 2, 3, 4, 5 or more times daily. Preferably 3 doses are taken daily. Most preferably, the doses are taken at meal times. The dosages may be taken orally in any suitable unit dosage form, such as pills, tablets, and capsules. Preferred are capsules made from gelatin.

As used herein, the term "carrier" denotes a solid or liquid filler, diluent, or encapsulating substance. Some examples of the substances that can act as carriers are sugars, such as lactose, glucose, and sucrose; starches, such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils, such as peanut oil, cottonseed oil, sesame oil, olive oil, corn oil and of the broma; polyols, such as propylene glycol, glycerin, sorbitol, mannitol, and polyethylene glycol; agar; alginic acid; pyrogen-free water; isotonic saline; ethyl alcohol and phosphate buffer solutions, as well as other non-toxic compatible substances used in preparation of formulations. Wetting agents and lubricants, such as sodium lauryl sulfate, as well as coloring agents, flavoring agents, and preservatives can also be present. Dye stuffs or pigments may be added to the tablets, for example, for identification or in order to characterize combinations of active doses.

Other preparations that can be used orally include push-fit capsules made of gelatin, as well as soft, sealed capsules made of gelatin and a plasticizer, such as glycerol or sorbitol. The push-fit capsules can contain the active compounds in the form of granules, which may be mixed with fillers, such as lactose, binders, such as starches, and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers or preservatives, such as Covitol F-1000, a solution of mixed tocopherols, available from Cognis, Ontario, Canada, may be added.

Powders are prepared by comminuting the compositions of the present invention to a suitable fine size and mixing with a similarly comminuted diluent pharmaceutical carrier, such as an edible carbohydrate material as for example, starch. Sweetening, flavoring, preservative, dispersing and coloring agents can also be present.

Capsules are made by preparing a powder mixture, as described above, and filling formed gelatin sheaths. A lubricant, such as talc, magnesium stearate, and calcium stearate can be added to the powder mixture as an adjuvant before the filling operation, a glidant, such as colloidal silica may be added to improve flow properties, and a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compositions of the present invention, suitably comminuted, with a diluent or base, such as starch, sucrose, kaolin, dicalcium phosphate, and the like. The powder mixture can be granulated by wetting with a binder, such as syrup, starch paste, acacia mucilage or solutions of cellulosic or polymeric materials, and forcing through a screen. As an alternative to granulating, the powder mixture can be run through the tablet machine, and the resulting imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The active ingredients can also be combined with free flowing inert carriers, and compressed into tablets directly without going through the granulating or slugging steps. A protective coating consisting of a sealing coat of shellac, a coating of sugar or polymeric material, and a polish coating of wax can be provided. Dye stuffs or pigments may be added to the tablets, for example, for identification or in order to characterize combinations of active doses. In tablet form the carrier comprises from about 0.1 percent to about 99.9 percent by weight of the total composition.

The following examples are provided for illustrative purposes only. They are not intended, and should not be interpreted to limit the scope of the invention, which is more fully set forth in the claims which follow thereafter.

EXAMPLES

Example 1

The ability of the dietary supplements black cohosh powder, black cohosh powder extract, echinacea, phytosterols, and astaxanthin to inhibit human aromatase enzyme activity was tested. The astaxanthin was obtained from Cyanotech Corporation, Kailua-Kona, Hi., the phytosterols were obtained from Archer Daniel Midland Corporation, Decatur, Ill., and the black cohosh and echinacea were obtained from Triarco Industries, Inc. As discussed above, human aromatase (CYP19) converts $C_{19}$ androgens to aromatic $C_{18}$ estrogenic steroids, and, thus, aromatase inhibitors have been used to treat postmenopausal breast cancer and other estrogen-dependent diseases. The inhibition of aromatase activity was measured in 96 well plates with cDNA-derived enzymes in microsomes prepared from baculovirus-infected insect cells.

Dibenzylfluorescien (DBF) was used as a reporter substrate for the activity of the aromatase enzyme. The storage and preparation conditions for the test substances are provided in Table 1.

TABLE 1

| Compound | Solvent | Storage Solid | Storage Solution |
|---|---|---|---|
| Black Cohosh Powder | DMSO | Room Temp | Refrigerated |
| Black Cohosh Powder Extract | DMSO | Room Temp | Refrigerated |
| Echinacea | DMSO | Room Temp | Refrigerated |
| Phytosterols | DMSO | Room Temp | Refrigerated |
| Astaxanthin | DMSO | Refrigerated | Refrigerated |

In the inhibition study, the 50 percent inhibitory concentration ($IC_{50}$) for each substance was determined with the enzyme. A single concentration of DBF, below the apparent $K_m$, and multiple test substance concentrations, separated by approximately ½ log, were tested in duplicate. Metabolism of the model substrate was assayed by the production of fluorescein metabolite, which was detected and measured using fluorescence.

The test substances were added to DMSO solvent, and the solid or stock solutions were stored as described in Table 1. The amount of solvent during the assay incubations was the same for all test substance concentrations.

The test solutions were prepared by adding the test substances to separate aliquots of dimethyl sulfoxide (DMSO). The target concentration of each test substance was 50 mg/ml. However, only black cohosh powder extract and astaxanthin would dissolve completely. Mild heat and sonication were applied to aid in obtaining solutions of the other substances at the desired concentration. The black cohosh powder and echinacea were also centrifuged prior to the use of the supernatant in the assay to sediment any particulate matter present in the solutions.

Except for the phytosterols, each test substance solution exhibited a color, indicating at least partial solution. As the phytosterols exhibited little or no solubility in DMSO, attempts to dissolve the phytosterols in alternate organic solvents compatible with the assay were made. None were successful. Visual inspection showed that at least partial solubilization of the phytosterols was obtained by diluting 50 mg/ml of the sterols in DMSO in increments to 2 mg/ml. Insoluble material that would not sediment when centrifuged was still present at 2 mg/ml, forming a thin, whitish layer on the surface of the solution. This particulate material was avoided when sampling the sterol solution for the assay.

As noted above, the assay was conducted in 96 well microplates. Initially, solutions of the substrate in acetonitrile at a concentration equal to the $k_m$ were prepared. The inhibition of the CYP19-catalyzed dealkylation of DBF was determined, using 4-hydroxyandrostenedione, a known inhibitor of CYP19, as a positive control, and sulfaphenazone, as a negative control. The final concentration of CYP19 (Gentest catalog number P260) was 0.4 pmol/well, and the final concentration of microsomal protein was normalized to 0.25 mg/ml by the addition of the insect cell control protein. The final concentration of substrate was 0.2 µM, and the final concentration of the potassium phosphate buffer was 50 µM. The incubation time was 30 minutes.

A row of 12 wells was used in each test, and each test of a test substance/substrate combination was duplicated in a second row. In each test, wells 1 to 8 contained serial 1:3 dilutions of the inhibitors in which the maximum concentration of phytosterols was 10 µg/ml, and that of the other test substances was 250 µg/ml, assuming complete solubilization at the desired concentrations, i.e., 2 mg/ml for the phytosterols and 50 mg/ml for the other test substances. Wells 9 and 10 contained no inhibitor, and wells 11 and 12 were blanks in which stop solution was added before the enzyme to test for background fluorescence.

After the buffer, cofactors, insect cell control protein, and test substances were added, where the control protein was added in an amount sufficient to improve solubility. The plates were then warmed to 37° C., and incubation was initiated by the addition of the pre-warmed enzyme, additional insect cell control protein in an amount sufficient to provide the desired concentration, and substrate. The final cofactor concentrations were 1.3 µM NADP, 3.3 µM glucose-6-phosphate, and 0.4 U/ml glucose-6-phosphate dehydrogenase. The incubation reactions were stopped after 30 minutes by the addition of 0.075 ml of 2 N NaOH, and fluorescence was measured for each well using a FLUOstar model 403 plate scanner after a post-stop incubation period of about 4 hours. The DBF metabolite fluorescein was measured using an excitation wavelength of about 485 nm and an emission wavelength of about 538 nm.

The $IC_{50}$ values obtained from the measurements are provided for each of the tests and duplicate tests in units of mg/ml for the test substances and in µM for the controls in Table 2. The results are consistent with a properly functioning model. All of the test compounds inhibited aromatase activity with astaxanthin and black cohosh demonstrating the most significant inhibition.

TABLE 2

Summary of $IC_{50}$ values. Data represent duplicate determinations, and are in units of µg/ml. Sulfaphenazole and 4-Hydroxandrostendione results are expressed in units of micromolar.

| Test Substance | CYP19/DBF |
|---|---|
| Black Cohosh Powder | >250, >250 |
| Black Cohosh Powder Extract | >250, >250 |
| Echinacea | >250, >250 |
| Phytosterols | >10, >10 |
| Astaxanthin | 67, 66 |
| Sulfaphenazole | >10, >10 |
| 4-Hydroxandrostendione | 0.011, 0.011 |

Example 2

An aromatase inhibiting dietary supplement composition comprising 500 mg black cohosh powder, 22 mg astaxanthin (5 percent spray dried), 200 mg Lodex 10, 14 mg magnesium stearate, and 14 mg silica was prepared.

Example 3

An aromatase inhibiting dietary supplement composition comprising 500 mg black cohosh powder, 250 mg phytosterols, 22 mg astaxanthin (5 percent spray dried), 200 mg Lodex, 10, 14 mg magnesium stearate, and 14 mg silica was prepared.

Example 4

An aromatase inhibiting dietary supplement composition comprising 500 mg black cohosh powder, 250 mg phytosterols, 22 mg astaxanthin (5 percent spray dried), 100 mg echinacea (PE 4 percent), 200 mg Lodex 10, 14 mg magnesium stearate, and 14 mg silica was prepared.

Example 5

An aromatase inhibiting dietary supplement composition comprising 20 mg black cohosh (PE 4:1), 22 mg astaxanthin (5 percent spray dried), 200 mg Lodex 10, 14 mg magnesium stearate, and 14 mg silica was prepared.

Example 6

An aromatase inhibiting dietary supplement composition comprising 20 mg black cohosh (PE 4:1), 22 mg astaxanthin (5 percent spray dried), 200 mg Lodex 10, 14 mg magnesium stearate, and 14 mg silica was prepared.

Example 7

An aromatase inhibiting dietary supplement composition comprising 20 mg black cohosh (PE 4:1), 250 mg phytosterols, 22 mg astaxanthin (5 percent spray dried), 100 mg echinacea (PE 4 percent), 200 mg Lodex 10, 14 mg magnesium stearate, and 14 mg silica was prepared.

Example 8

An aromatase inhibiting dietary supplement composition comprising 20 mg black cohosh (PE 4:1), 10 mg astaxanthin (10 percent oleoresin), 295 mg soybean oil, 24 mg beeswax, 1 mg soy lecithin, and 0.30 mg Covitol F-1000 was prepared.

Example 9

An aromatase inhibiting dietary supplement composition comprising 20 mg black cohosh (PE 4:1), 10 mg astaxanthin (10 percent oleoresin), 25 mg phytosterols, 420 mg soybean oil, 24 mg beeswax, 1 mg soy lecithin, and 1.0 mg Covitol F-1000 was prepared.

Example 10

An aromatase inhibiting dietary supplement composition comprising 20 mg black cohosh (PE 4:1), 10 mg astaxanthin (10 percent oleoresin), 25 mg phytosterols, 50 mg echinacea (PE 4 percent), 770 mg soybean oil, 23 mg beeswax, 1 mg soy lecithin, and 1.0 mg Covitol F-1000 was prepared.

This invention is not limited by the embodiments disclosed herein, and it will be appreciated that numerous modifications and embodiments may be devised by those skilled in the art. Therefore, it is intended that the appended claims cover all such modifications and embodiments that fall within the true spirit and scope of the present invention.

What is claimed is:

1. A method of administering to a subject a dietary supplement composition consisting of astaxanthin, black cohosh, echinacea, and phytosterols.

\* \* \* \* \*